(12) United States Patent
Vandyck et al.

(10) Patent No.: US 9,156,839 B2
(45) Date of Patent: Oct. 13, 2015

(54) FUSED BICYCLIC SULFAMOYL DERIVATIVES AND THE USE THEREOF AS MEDICAMENTS FOR THE TREATMENT OF HEPATITIS B

(71) Applicant: JANSSEN SCIENCES IRELAND UC, Little Island, Co Cork (IE)

(72) Inventors: Koen Vandyck, Paal-Beringen (BE); Wim Gaston Verschueren, Berchem (BE); Pierre Jean-Marie Bernard Raboisson, Rosieres (BE)

(73) Assignee: JANSSEN SCIENCES IRELAND UC, Little Island, Co Cork (IE)

( * ) Notice: Subject to any disclaimer, the term of this patent is extended or adjusted under 35 U.S.C. 154(b) by 0 days.

(21) Appl. No.: 14/424,280

(22) PCT Filed: Aug. 28, 2013

(86) PCT No.: PCT/EP2013/067814
§ 371 (c)(1),
(2) Date: Feb. 26, 2015

(87) PCT Pub. No.: WO2014/033167
PCT Pub. Date: Mar. 6, 2014

(65) Prior Publication Data
US 2015/0218159 A1    Aug. 6, 2015

(30) Foreign Application Priority Data

Aug. 28, 2012  (EP) ..................................... 12182078

(51) Int. Cl.
| | | |
|---|---|---|
| C07D 231/56 | (2006.01) |
| C07D 261/20 | (2006.01) |
| A61K 31/416 | (2006.01) |
| C07D 471/04 | (2006.01) |
| A61K 31/423 | (2006.01) |
| C07D 405/12 | (2006.01) |
| A61K 31/437 | (2006.01) |
| A61K 45/06 | (2006.01) |

(52) U.S. Cl.
CPC ............ *C07D 471/04* (2013.01); *A61K 31/416* (2013.01); *A61K 31/423* (2013.01); *A61K 31/437* (2013.01); *A61K 45/06* (2013.01); *C07D 231/56* (2013.01); *C07D 261/20* (2013.01); *C07D 405/12* (2013.01)

(58) Field of Classification Search
None
See application file for complete search history.

(56) References Cited

U.S. PATENT DOCUMENTS 8,629,274 B2 * 1/2014 Hartman et al. .................. 546/1

FOREIGN PATENT DOCUMENTS

| WO | WO 03/002518 A1 | 1/2003 |
| WO | WO 2013/006394 A1 | 1/2013 |
| WO | WO 2013/096744 A1 | 6/2013 |

OTHER PUBLICATIONS

Weber, O., et al., "Inhibition of Human Hepatitis B Virus (HBV) by a Novel Non-Nucleosidic Compound in a Transgenic Mouse Model", Antiviral Research, vol. 43, pp. 69-78 (2002).
European Search Report completed Oct. 10, 2012 for corresponding Application No. EP12182078.
International Search Report mailed Oct. 11, 2013 for corresponding Application No. PCT/EP2013/067814.

* cited by examiner

*Primary Examiner* — Kamal Saeed
(74) *Attorney, Agent, or Firm* — Bradley E. Davis

(57) ABSTRACT

Inhibitors of HBV replication of Formula (I)

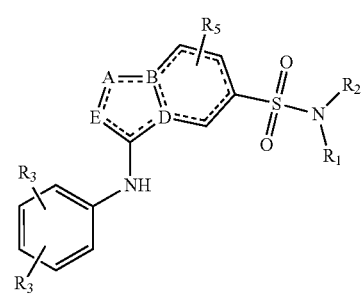

including stereochemically isomeric forms, and salts, hydrates, solvates thereof, wherein A-E, $R_1$, $R_2$, $R_3$ and $R_5$, have the meaning as defined herein.
The present invention also relates to processes for preparing said compounds, pharmaceutical compositions containing them and their use, alone or in combination with other HBV inhibitors, in HBV therapy.

11 Claims, No Drawings

FUSED BICYCLIC SULFAMOYL DERIVATIVES AND THE USE THEREOF AS MEDICAMENTS FOR THE TREATMENT OF HEPATITIS B

This application is a 35 U.S.C. §371 nationalization of PCT application PCT/EP2013/067814 filed Aug. 28, 2013, which claims priority to European patent application EP 12182078.1 filed Aug. 28, 2012, both of which are incorporated herein by reference.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

Heteroaryldihydropyrimidines (HAPs) were identified as a class of HBV inhibitors in tissue culture and animal models (Weber et al., Antiviral Res. 54: 69-78). Furthermore, WO2013/006394, published on Jan. 10, 2013, and WO2013/096744, published on Jun. 27, 2013 relate to subclasses of Sulphamoyl-arylamides active against HBV.

Amongst the problems which HBV direct antivirals may encounter are toxicity, mutagenicity, lack of selectivity, poor efficacy, poor bioavailability, and difficulty of synthesis.

There is a need for additional HBV inhibitors that may overcome at least one of these disadvantages.

DESCRIPTION OF THE INVENTION

In one aspect, the present invention provides compounds, which can be represented by Formula (I):

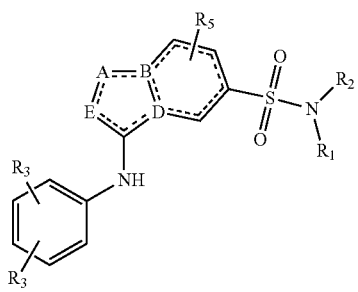

(I)

or a stereoisomer or tautomeric form thereof, wherein:

A represents N, C or O;

B represents C or N;

D represents C or N;

E represents C or N;

Wherein if A and E are either N or C, they are optionally substituted with $R_4$;

$R_1$ represents hydrogen or $C_1$-$C_3$alkyl;

$R_2$ represents $C_1$-$C_6$alkyl, $C_1$-$C_3$alkyl-$R_6$, benzyl, or a 3-7 membered saturated ring optionally containing one or more heteroatoms each independently selected from the group consisting of O, S and N, such $C_1$-$C_6$alkyl or a 3-7 membered saturated ring optionally being substituted with one or more substituents each independently selected from the group consisting of of hydrogen, halo, $C_1$-$C_3$alkyloxy, $C_1$-$C_4$alkyl, OH, CN, $CFH_2$, $CF_2H$ or $CF_3$;

Or $R_1$ $R_2$ together with the Nitrogen to which they are attached form a 5-7 membered saturated ring optionally being substituted with one or more substituents each independently selected from the group consisting of of hydrogen, halogen, $C_1$-$C_4$alkyloxy, $C_1$-$C_3$alkyl, OH, CN, $CFH_2$, $CF_2H$ and $CF_3$;

Each $R_3$ is independently selected from hydrogen, halo, $C_1$-$C_4$alkyloxy, $C_1$-$C_4$alkyl, OH, CN, $CFH_2$, $CF_2H$, $CF_3$ or a 3-5 membered saturated ring optionally containing one or more heteroatoms each independently selected from the group consisting of O and N;

$R_4$ represents hydrogen, $C_1$-$C_4$alkyl, $C_3$-$C_5$cycloalkyl, —(C=O)$C_1$-$C_4$-alkyl, —(C=O)—$C_1$-$C_3$alkyloxy or in case A or E equals C, $R_4$ in addition can be halogen;

$R_5$ represents hydrogen or Halogen;

$R_6$ represents a 3-7 membered saturated ring optionally containing one or more heteroatoms each independently selected from the group consisting of O, S and N, such 3-7 membered saturated ring optionally being substituted with one or more substituents each independently selected from the group consisting of hydrogen, halo, $C_1$-$C_3$alkyloxy, $C_1$-$C_4$alkyl, OH, CN, $CFH_2$, $CF_2H$, $CF_3$;

or a pharmaceutically acceptable salt or solvate thereof.

The invention further relates to a pharmaceutical composition comprising a compound of Formula (I), and a pharmaceutically acceptable carrier.

The invention also relates to the compounds of Formula (I) for use as a medicament, preferably for use in the prevention or treatment of an HBV infection in a mammal In a further aspect, the invention relates to a combination of a compound of Formula (I), and another HBV inhibitor.

DEFINITIONS

The term "$C_{1-3}$alkyl" or "$C_1$-$C_3$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-}C_3$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl. $C_{1-4}$alkyl as a group or part of a group defines straight or branched chain saturated hydrocarbon radicals having from 1 to 4 carbon atoms such as the group defined for $C_{1-3}$alkyl and butyl and the like $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like The term "$C_{1-3}$alkyloxy" as a group or part of a group refers to a radical having the Formula —$OR_c$ wherein $R_c$ is $C_{1-3}$alkyl. Non-limiting examples of suitable $C_{1-3}$alkyloxy include methyloxy (also methoxy), ethyloxy (also ethoxy), propyloxy and isopropyloxy.

As used herein, the term "3-7 membered saturated ring" means saturated cyclic hydrocarbon with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms, such that at least one carbon atom is replaced by a heteroatom selected from N, O and S, in particular from N and O. Examples include oxetane, tetrahydro-2H-pyranyl, piperidinyl, tetrahydrofuranyl, morpholinyl and pyrrolidinyl.

As used herein

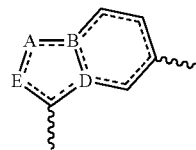

means a fused bicyclic group optionally containing one or more heteroatoms, such that at least B, D or E is replaced by nitrogen or A by N or O ((hetero-)aryl). The indicated (hetero-) aryl group need to only have some degree of aromatic character. Illustrative examples of (hetero-) aryl groups include, but are not limited to benzofuran, indole, isoindole, indazole, imidazopyridine and benzisoxazole. Preferred are benzisoxazole and indazole.

It should be noted that different isomers of the various heterocycles may exist within the definitions as used throughout the specification. For example, pyrrolyl may be 1H-pyrrolyl or 2H-pyrrolyl.

The term halo is generic to fluoro, chloro, bromo or iodo.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

When any variable (e.g. halogen or $C_{1-4}$alkyl) occurs more than one time in any constituent, each definition is independent.

For therapeutic use, the salts of the compounds of formula (I) are those wherein the counter ion is pharmaceutically or physiologically acceptable. However, salts having a pharmaceutically unacceptable counter ion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diasteromeric racemates of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

DETAILED DESCRIPTION OF THE INVENTION

Whenever used hereinafter, the term "compounds of formula (I)",

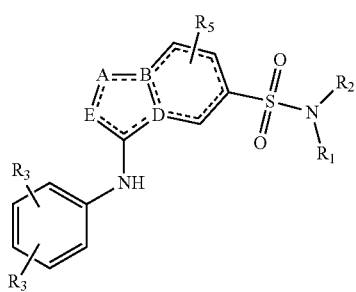

or "the present compounds" or similar term is meant to include the compounds of general formula (I) (Ia), (Ib), (I-I), (I-II) salts, stereoisomeric forms and racemic mixtures or any subgroups thereof.

According to the invention, in formula (I),
A represents N, C or O;
B represents C or N;
D represents C or N;
E represents C or N;
Wherein if A and E are either N or C, they are optionally substituted with $R_4$;
$R_1$ represents hydrogen or $C_1$-$C_3$alkyl;
$R_2$ represents $C_1$-$C_6$alkyl, $C_1$-$C_3$alkyl-$R_6$, benzyl, or a 3-7 membered saturated ring optionally containing one or more heteroatoms each independently selected from the group consisting of O, S and N, such $C_1$-$C_6$alkyl or a 3-7 membered saturated ring optionally being substituted with one or more substituents each independently selected from the group consisting of of hydrogen, halo, $C_1$-$C_3$alkyloxy, $C_1$-$C_4$alkyl, OH, CN, $CFH_2$, $CF_2H$ or $CF_3$;
Or $R_1$ $R_2$ together with the Nitrogen to which they are attached form a 5-7 membered saturated ring optionally being substituted with one or more substituents each independently selected from the group consisting of of hydrogen, halogen, $C_1$-$C_4$alkyloxy, $C_1$-$C_3$alkyl, OH, CN, $CFH_2$, $CF_2H$ and $CF_3$;
Each $R_3$ is independently selected from hydrogen, halo, $C_1$-$C_4$alkyloxy, $C_1$-$C_4$alkyl, OH, CN, $CFH_2$, $CF_2H$, $CF_3$ or a 3-5 membered saturated ring optionally containing one or more heteroatoms each independently selected from the group consisting of O and N;
$R_4$ represents hydrogen, $C_1$-$C_4$alkyl, $C_3$-$C_5$cycloalkyl, —(C=O)$C_1$-$C_4$-alkyl, —(C=O)—$C_1$-$C_3$alkyloxy or in case A or E equals C, $R_4$ in addition can be halogen;
$R_5$ represents hydrogen or Halogen and
$R_6$ represents a 3-7 membered saturated ring optionally containing one or more heteroatoms each independently selected from the group consisting of O, S and N, such 3-7 membered saturated ring optionally being substituted with one or more substituents each independently selected from the group consisting of hydrogen, halo, $C_1$-$C_3$alkyloxy, $C_1$-$C_4$alkyl, OH, CN, $CFH_2$, $CF_2H$, $CF_3$.

In a first embodiment of the invention, $R_4$ represents hydrogen, $C_3$-$C_5$cycloalkyl, —(C=O)$C_1$-$C_4$-alkyl, —(C=O)—$C_1$-$C_3$alkyloxy or in case A or E equals C, $R_4$ in addition can be halogen.

In one embodiment of the invention, $R_1$ represents hydrogen or methyl. In a second embodiment of the present invention, $R_2$ represents $C_1$-$C_3$alkyl-$R_6$ or $C_4$-$C_7$ cycloalkyl, optionally being substituted with one or more substituents each independently selected from the group consisting of of hydrogen, halo, $C_1$-$C_3$alkyloxy, $C_1$-$C_4$alkyl, OH, CN, $CFH_2$, $CF_2H$, $CF_3$ And wherein $R_6$ represents a $C_4$-$C_7$ cycloalkyl, optionally being substituted with one or more substituents each independently selected from the group consisting of of hydrogen, halo, $C_1$-$C_3$alkyloxy, $C_1$-$C_4$alkyl, OH, CN, $CFH_2$, $CF_2H$, $CF_3$ In a third embodiment, $R_2$ represents $C_4$-$C_7$ cycloalkyl, optionally being substituted with one or more substituents each independently selected from the group consisting of of hydrogen, halo, $C_1$-$C_3$alkyloxy, $C_1$-$C_4$alkyl, OH, CN, $CFH_2$, $CF_2H$, $CF_3$. In yet another embodiment, $R_2$ represents $C_5$-cycloalkyl or $C_6$-cycloalkyl, optionally being substituted with one or more substituents each independently selected from the group consisting of of hydrogen, halo, and $C_1$-$C_4$alkyl.

In another embodiment $R_3$ represents Fluor, $C_1$-$C_3$alkyl or cyclopropyl. Preferably, at least one $R_3$ represents methyl, i-propyl or cyclopropyl. In another embodiment, one $R_3$ represents methyl, i-propyl or cyclopropyl and the other $R_3$ represents Fluor, or hydrogen.

Preferably, $R_4$ represents hydrogen.

In a preferred embodiment, the compounds are represented by Formula (I-I) or (I-II)

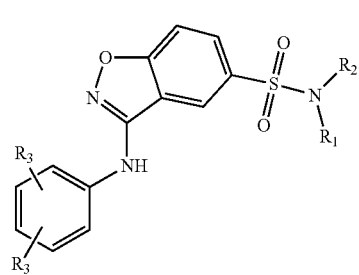

(I-I)

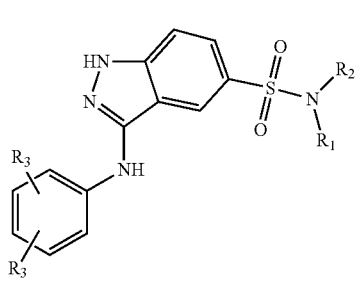

(I-II)

wherein $R_1$, $R_2$, $R_3$ are defined as above.

Further combinations of any of the sub- or preferred embodiments are also envisioned to be in the scope of the present invention.

Most preferred are the compounds as shown in table 1.

In a further aspect, the present invention concerns a pharmaceutical composition comprising a therapeutically or prophylactically effective amount of a compound of Formula (I) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (I), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (I) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of Formula (I) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of Formula (I).

The compounds of Formula (I), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of formula (I) or any subgroup thereof, as specified herein with other anti-HBV agents. The term "combination" may relate to a product or kit containing (a) a compound of Formula (I), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of formula (I) or any subgroup thereof with at least one anti-HBV agent. In a particular embodiment, the invention concerns combination of a compound of formula (I) or any subgroup thereof with at least two anti-HBV agents. In a particular embodiment, the invention concerns combination of a compound of formula (I) or any subgroup thereof with at least three anti-HBV agents. In a particular embodiment, the invention concerns combination of a compound of formula (I) or any subgroup thereof with at least four anti-HBV agents.

The combination of previously known anti-HBV agents, such as interferon-α (IFN-α), pegylated interferon-α, 3TC, adefovir or a combination thereof, and, a compound of formula (I) or any subgroup thereof can be used as a medicine in a combination therapy.

General Synthetic Methods

Generic Synthesis:

Compounds of general formula (Ia) (compound I where E equals Nitrogen and B and D equal carbon, with A equals nitrogen or oxygen, scheme 1) can be synthesized as shown in scheme 1. A 5-(chlorosulfonyl)-2-fluorobenzoic acid derivative II is coupled with an amine of structure III, resulting in sulfonamide IV. Via a amide formation between carboxylic acid IV and aniline V, for example by using HATU in the presence of an organicbase like N,N-diisopropyethylamine (DIPEA) in DMF, compound VI is obtained. Thioamide VII can be obtained via reaction of VI with a thiation agent like the Lawesson's reagent (2,4-bis(4-methoxyphenyl)-1,3,2,4-dithiadiphosphetane-2,4-disulfide). Finally compound VII is reacted with $NH_2OH$ in case A equals oxygen or $NH_2NH_2$ in case A equals nitrogen, at higher temperature (for example 120°-150° C. in DMSO) resulting in compound Ia.

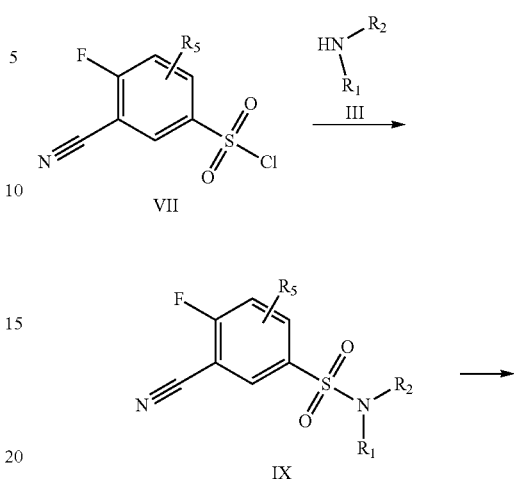

Scheme 2

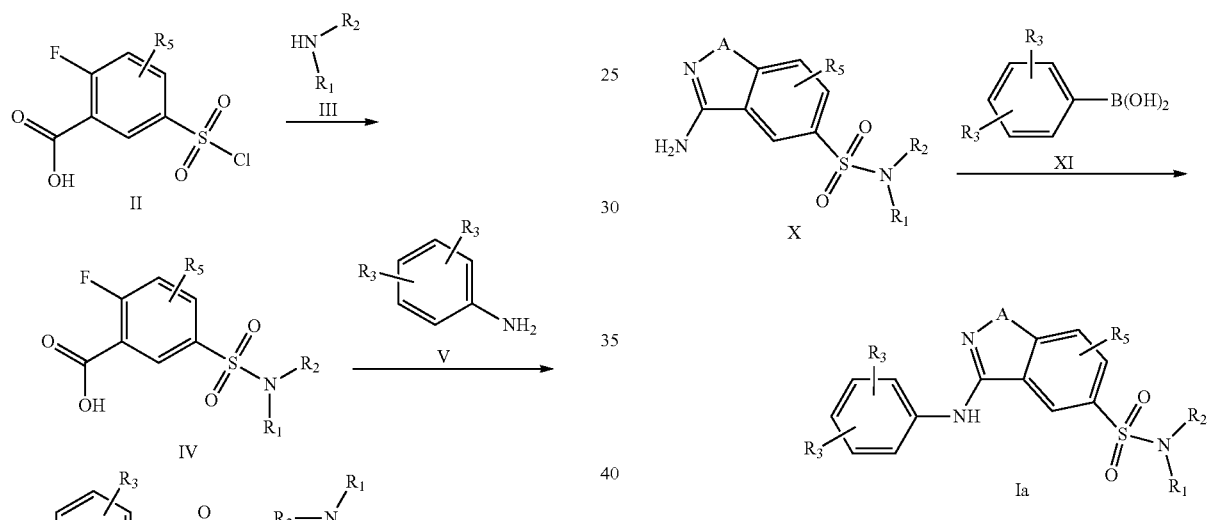

Scheme 1

Alternatively, for the synthesis of compounds of general formula (Ia), the route as described in scheme 2, can be used. Compound VIII can be reacted with an amine of formula (III), resulting in compound IX, which is cyclized to a compound of formula X, for example by using hydrazine in iPrOH at 110° C. when A equals NH in compound X. Compound X can be further transformed to a compound of general formula (Ia), for example by a copper catalyzed coupling with the use of a boronic acid XI.

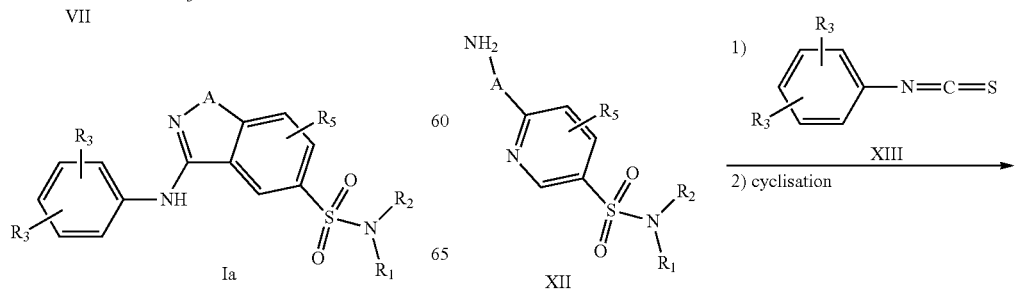

Scheme 3

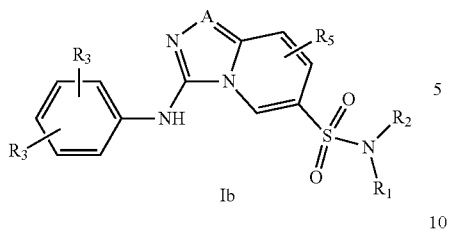

Ib

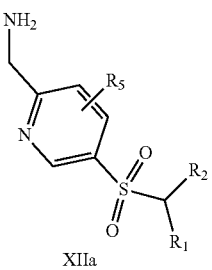

XIIa

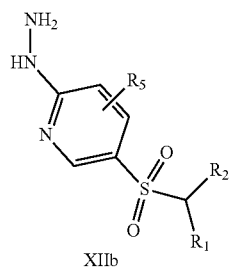

XIIb

Scheme 3 describes the general synthesis of compounds of general formula (Ib). By reacting compound XII with an thioisocyanate XIII and cyclising the formed intermediate to compound of general formula (Ib), for example under the influence of N,N'-dicyclohexylmethanediimine or 2-chloro-1-methylpyridinium iodide. The compounds of general formula XIIa and XIIb can be prepared as shown in scheme 4 and as exemplified in the synthesis of compound 17, 18 and 19.

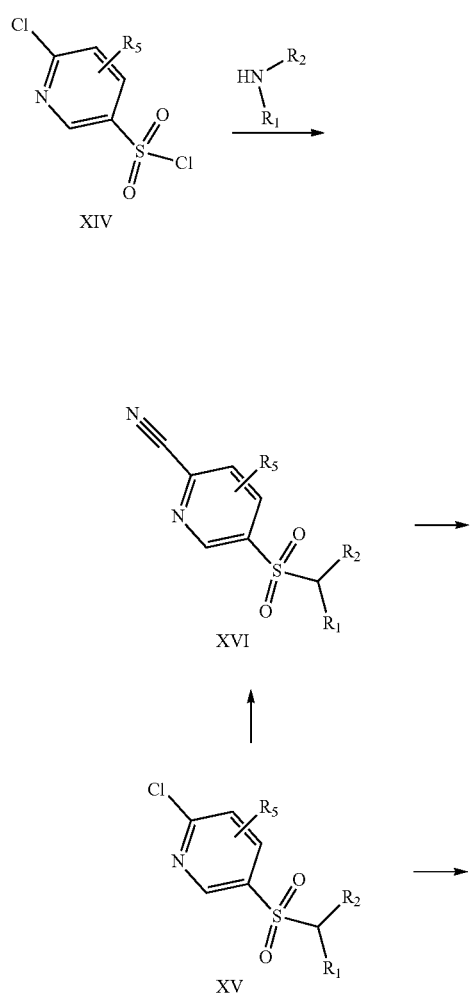

Scheme 4

EXPERIMENTAL

LCMS Conditions

Method A:
General: mobile phase A: $H_2O$ (0.1% TFA; B: $CH_3CN$ (0.05% TFA) Stop Time: 2 min; gradient time (min) [% A/% B] 0.01 [90/10] to 0.9 [20/80] to 1.5[20/80] to 1.51 [90/10]; flow: 1.2 mL/min; column temp.: 50° C., Xtimate C18 2.1*30 mm, 3 µm.

Method B:
General: mobile phase A: $H_2O$ (0.1% TFA; B: $CH_3CN$ (0.05% TFA) Stop Time: 10 min; gradient time (min) [% A/% B] 0.0 [90/10] to 0.8 [90/10] to 4.5 [20/80] to 7.5 [20/80] to 8.0 [90/10]; flow: 0.8 mL/min; column temp.: 50° C., YMC-PACK ODS-AQ, 50×2.0 mm, 5 µm.

Method C:
General: mobile phase A: $H_2O$ (0.1% TFA; B: $CH_3CN$ (0.05% TFA) Stop Time: 10 min; gradient time(min) [% A/% B] 0.0 [70/30] to 0.8 [70/30] to 4 [10/90] to 7.5 [10/90] to 8.0 [70/30]; flow: 0.8 mL/min; column temp.: 50° C. YMC-PACK ODS-AQ, 50×2.0 mm, 5 µm.

Method D:
General: mobile phase A: $H_2O$ (0.1% TFA; B: $CH_3CN$ (0.05% TFA) Stop Time: 10 min; gradient time (min) [% A/% B] 0.0 [100/0] to 1 [100/0] to 5 [40/60] to 7.5 [40/60] to 8.0 [100/0]; flow: 0.8 mL/min; column temp.: 50° C., YMC-PACK ODS-AQ, 50×2.0 mm 5 µm.

Method E:
General: mobile phase A: $H_2O$ (0.1% TFA); B: $CH_3CN$ (0.05% TFA) Stop Time: 10 min; gradient time(min) [% A/% B] 0.0 [90/10] to 0.8 [90/10] to 4.5 [20/80] to 7.5 [20/80]; 9.5 [90/10] flow: 0.8 mL/min; column temp.: 50 C, Agilent TC-C18, 50×2.1 mm, 5 µm Method F:
The LC measurement was performed using an Acquity UPLC (Waters) with column heater (set at 55° C.). Reversed phase UPLC (Ultra Performance Liquid Chromatography) was carried out on a Acquity UPLC HSS T3 column (1.8 µm, 2.1×100 mm; Waters Acquity) with a flow rate of 0.8 mL/min. Two mobile phases (A: 10 mM ammonium acetate in $H_2O$/acetonitrile 95/5; mobile phase B: acetonitrile) were used to run a gradient condition from 100% A and 0% B to 5% A and 95% B in 2.1 minutes and subsequently to 0% A and 100% B in 0.9 minutes to 5% A and 95% B in 0.5 min. An injection volume of 1 μl was used. Cone voltage was 30 V for positive ionization mode and 30 V for negative ionization mode.

Synthesis of compounds:

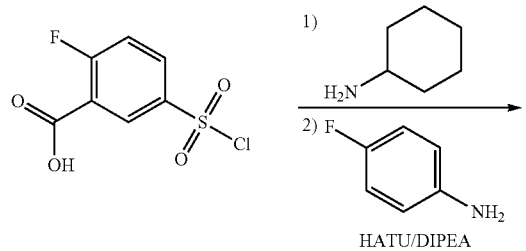

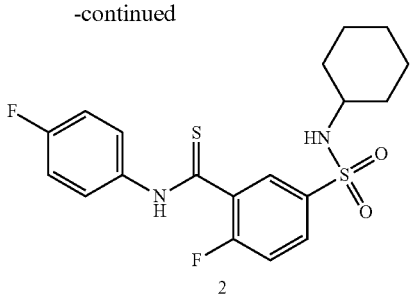

A mixture of compound 1 (1.5 g, 3.8 mmol) and 2,4-bis(4-methoxyphenyl)-1,3,2,4-dithiadiphosphetane-2,4-disulfide (Lawesson's reagent 923 mg, 2.28 mmol) in toluene (40 mL) was stirred at 110° C. for 15 hours. The mixture was concentrated in vacuo resulting in a yellow solid (2.2 g). This solid, containing compound 2, was used as such in the next reaction.

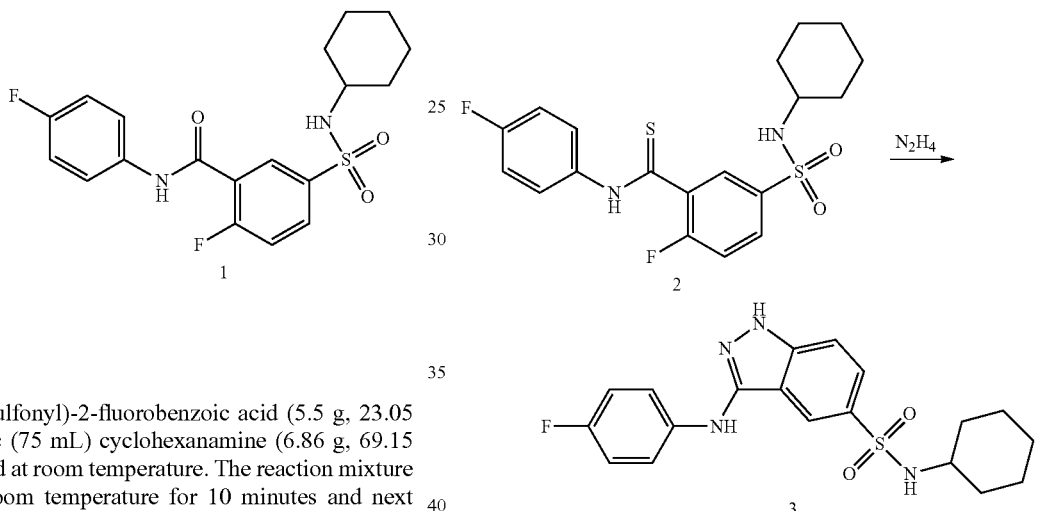

To 5-(chlorosulfonyl)-2-fluorobenzoic acid (5.5 g, 23.05 mmol) in EtOAc (75 mL) cyclohexanamine (6.86 g, 69.15 mmol) was added at room temperature. The reaction mixture was stirred at room temperature for 10 minutes and next washed with 1N HCl (50 mL). The organic phase was dried over MgSO₄ and concentrated in vacuo, resulting in a white solid (6 g) containing 5-(N-cyclohexylsulfamoyl)-2-fluorobenzoic acid, which was used as such in the next step without further purification. To part of the above obtained solid (1.5 g), 4-fluoroaniline (553 mg, 4.98 mmol) and DIPEA (1.287 g, 9.96 mmol) in DMF (30 mL), HATU (2.27 g, 5.97 mmol) was added at room temperature. The mixture was stirred at room temperature for 15 hours. EtOAc (300 mL) and water (200 mL) were added and the mixture was washed with brine (2×200 mL), dried over MgSO₄, filtered and concentrated resulting in compound 1. Method A; Rt: 1.12 min. m/z: 395.1 (M+H)⁺ Exact mass: 394.1;

Part of the above obtained solid containing compound 2 (700 mg) and N₂H₄·H₂O (546 mg, 17 mmol) in DMSO (15 mL) was stirred at 150° C. for 5 hours. Water was added and the mixture was extracted with EtOAc (150 mL). The organic layers was washed with brine, dried and concentrated in vacuo, resulting in a residue. The obtained residue was recrystallised from MeOH-water resulting in compound 3 as light yellow solid (280 mg) after filtration and drying in vacuo. Method B; Rt: 4.52 min. m/z: 389.2 (M+H)⁺ Exact mass: 388.1; ¹H NMR (400 MHz, DMSO-d₆) δ ppm 12.41 (1H, s), 9.26 (1H, s), 8.60 (1H, d, J=1.0 Hz), 7.66-7.82 (3H, m), 7.41-7.62 (2H, m), 7.02-7.21 (2H, m), 2.78-3.04 (1H, m), 1.46-1.69 (4H, m), 1.32-1.46 (1H, m), 0.89-1.30 (5H, m)

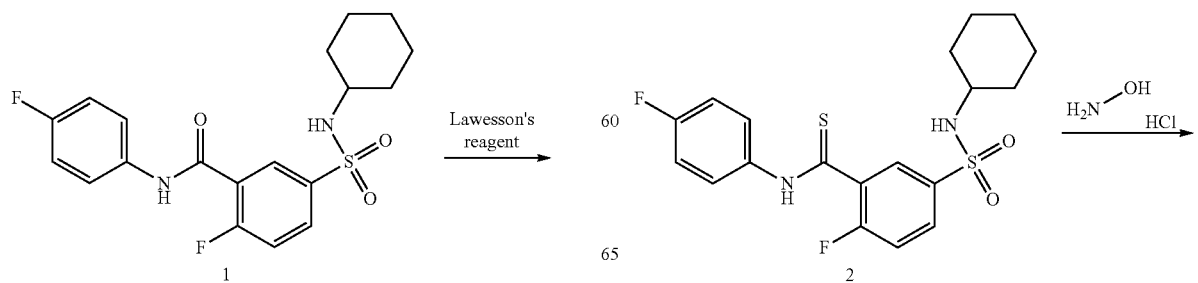

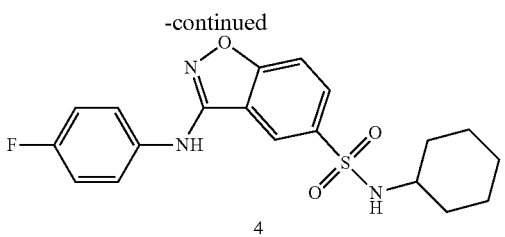

4

Part of the above obtained solid containing compound 2 (1 g), Na$_2$CO$_3$ (2.58 g, 24.3 mmol) and NH$_2$OH.HCl (1.69 g, 24.3 mmol) in DMSO (20 mL) and water (4 mL) was stirred at 120° C. for 5 hour. Water was added and the mixture was extracted with EtOAc (150 mL), the organic layer washed with brine, dried and concentrated in vacuo, resulting in a residue. This residue was purified by preparative HPLC (Phenomenex Synergi max-RP 150×30 mm; Mobile phase A: purified water (0.075% TFA, V/V); Mobile phase B: acetonitrile; Flow rate: 30 mL/min; Gradient: 53-83% over 8 minutes, resulting in compound 4 as a white solid (120 mg). Method C; Rt: 3.79 min. m/z: 390.3 (M+H)$^+$ Exact mass: 389.1; $^1$H NMR (400 MHz, DMSO-d$_6$) δ ppm 9.90 (1H, s), 8.75 (1H, d, J=1.5 Hz), 8.04 (1H, dd, J=9.0, 1.5 Hz), 7.83 (1H, d, J=9.0 Hz), 7.75 (1H, d, J=7.5 Hz), 7.67-7.73 (2H, m), 7.16-7.30 (2H, m), 2.90-3.02 (1H, m), 1.48-1.65 (4H, m), 1.37-1.49 (1H, m), 0.95-1.21 (5H, m)

Compound 5

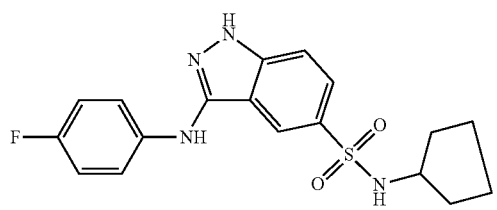

Cyclopentanamine (17.85 g, 210 mmol) and NaOH (16.8 g, 420 mmol) were dissolved in THF (300 mL) and H$_2$O (300 mL). 5-(chlorosulfonyl)-2-fluorobenzoic acid (50 g, 210 mmol) was added at 0° C. The mixture was stirred at 20° C. for 12 hours. The mixture was washed with ethyl acetate (3×50 mL). The aqueous layer was separated and adjusted to pH=3 with 1N HCl. The formed precipitate was filtered and dried in vacuo resulting in 5-(N-cyclopentylsulfamoyl)-2-fluorobenzoic acid (40 g). 5-(N-cyclopentylsulfamoyl)-2-fluorobenzoic acid (40 g, 139.4 mmol), 4-fluoroaniline (19.3 g, 167.2 mmol) and triethylamine (28.2 g, 278.8 mmol) were dissolved in DMF (400 mL). HATU (63 g, 167.2 mmol) was added at 0° C. and the mixture was next stirred at 20° C. for 6 hours. The solvent was removed in vacuo and the obtained residue was purified by silica gel column chromatography (eluent: petroleum ether: ethyl acetate=5:1) resulting in 5-(N-cyclopentylsulfamoyl)-2-fluoro-N-(4-fluorophenyl)benzamide (38 g). 5-(N-cyclopentylsulfamoyl)-2-fluoro-N-(4-fluorophenyl)benzamide (38 g, 100 mmol) and Lawesson's reagent (40.4 g, 100 mmol) were dissolved in toluene (1000 mL). The mixture was stirred at 120° C. for 16 hours. The volatiles were removed in vacuo and the obtained residue and N$_2$H$_4$—H$_2$O (80 mL) were dissolved in 1,4-dioxane (500 mL). The mixture was stirred for 12 hours at 160° C. The solvent was removed in vacuo and the obtained residue was purified by high performance liquid chromatography (Column: Phenomenex Synergi Diamonsil 150*20 mm*5 um. Method: 25 to 55% B in A; A: H$_2$O+0.1% TFA B: CH$_3$CN. Flow Rate (mL/min): 40). The pure fractions were collected and basified to pH=7 with saturated aqueous NaHCO3. The organic volatiles were removed in vacuo and the aqueous layer was extracted with ethyl acetate (3×20 mL). The combined organic layers were washed with brine and dried over Na$_2$SO$_4$. The solvent was removed in vacuo, the obtained residue was suspended in water (5 mL) and the aqueous layer was lyophilized to dryness resulting in compound 5 (15 g). Method B; Rt: 4.14 min. m/z: 375.2 (M+H)$^+$; Exact mass: 374.1; $^1$H NMR (600 MHz, DMSO-d$_6$) δ ppm 1.26-1.33 (m, 2H), 1.33-1.40 (m, 2H), 1.49-1.56 (m, 2H), 1.56-1.61 (m, 2H), 3.40 (quin, J=6.6 Hz, 1H), 7.14 (t, J=8.1 Hz, 2H), 7.47 (br. s., 1H), 7.55 (d, J=8.8 Hz, 1H), 7.73 (dd, J=8.8, 1.8 Hz, 1H), 7.76 (dd, J=9.1, 4.8 Hz, 2H), 8.64 (d, J=1.6 Hz, 1H), 9.28 (s, 1H), 12.37 (br. s., 1H).

Compound 6

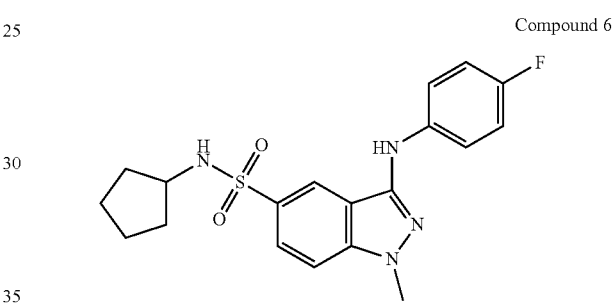

Compound 5 (400 mg, 1 mmol) was dissolved in DMF (50 mL). CH$_3$I (0.71 g, 5 mmol) and K$_2$CO$_3$ (0.69 g, 5 mmol) were added to the mixture. The mixture was stirred at 110° C. for 12 hours. The solvent was removed in vacuo. The residue was purified by high performance liquid chromatography (Column: Phenomenex Synergi Diamonsil 150*20 mm*5 um. Method: 25% to 55% B in A; A: H$_2$O+0.1% TFA B: CH$_3$CN. Flow Rate (mL/min): 40). The pure fractions were collected and basified to pH=7 with saturated aqueous NaHCO$_3$. The organic solvent was removed in vacuo and the aqueous layer was extracted with ethyl acetate (3×20 mL). The combined organic layers were washed with brine and dried over Na$_2$SO$_4$. The solvent was removed in vacuo. The residue was purified by thin layer chromatography (eluent: petroleum ether: ethyl acetate=1:1). The obtained product was suspended in water (5 mL) and CH$_3$CN (2 mL) and the mixture was lyophilized to dryness resulting in compound 6 (53 mg). Method D; Rt: 5.87 min. m/z: 389.2 (M+H)$^+$ Exact mass: 388.1; $^1$H NMR (400 MHz, DMSO-d$_6$) δ ppm 9.32 (1H, s), 8.58 (1H, s), 7.67-7.81 (3H, m), 7.58-7.67 (1H, m), 7.46 (1H, d, J=6.5 Hz), 7.12 (2H, t, J=8.8 Hz), 3.93 (3H, s), 3.33-3.40 (1H, m), 1.42-1.66 (4H, m), 1.16-1.42 (4H, m). $^1$H NMR (400 MHz, CHLOROFORM-d) δ ppm 8.26 (1H, d, J=1.0 Hz), 7.80 (1H, dd, J=8.9, 1.6 Hz), 7.46-7.55 (2H, m), 7.34 (1H, d, J=8.8 Hz), 7.03 (2H, t, J=8.7 Hz), 6.48 (1H, s), 4.46 (1H, d, J=7.0 Hz), 3.98 (3H, s), 3.52-3.66 (1H, m), 1.69-1.83 (2H, m), 1.57-1.66 (2H, m), 1.45-1.54 (2H, m), 1.26-1.45 (2H, m).

Compound 7

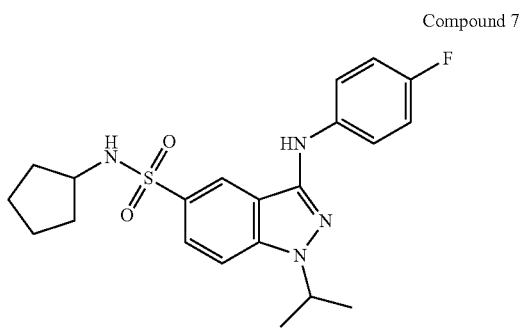 [SMILES: CC(C)n1nc(Nc2ccc(F)cc2)c2cc(S(=O)(=O)NC3CCCC3)ccc21]

Compound 5 (600 mg, 1.6 mmol) was dissolved in DMF (50 mL). 2-bromopropane (0.98 g, 8 mmol) and $K_2CO_3$ (0.45 g, 5 mmol) were added to the mixture at 0° C. The mixture was stirred at 0° C. for 1 hour. The solvent was removed in vacuo and the obtained residue was purified by high performance liquid chromatography (Column: Phenomenex Synergi Diamonsil 150*20 mm*5 um. Method: 25% to 55% B in A, A: $H_2O$+0.1% TFA B: $CH_3CN$. Flow Rate (mL/min): 40). The pure fractions were collected and basified to pH=7 with saturated aqueous $NaHCO_3$. The volatiles were removed in vacuo and the aqueous layer was extracted with ethyl acetate (3×20 mL). The combined organic layers were washed with brine and dried over $Na_2SO_4$. The solvent was removed in vacuo, the obtained residue was suspended in water (5 mL) and $CH_3CN$ (2 mL) and the mixture was lyophilized to dryness resulting in compound 7 (420 mg). Method E; Rt: 4.90 min. m/z: 417.1 (M+H)$^+$ Exact mass: 416.2. $^1$H NMR (600 MHz, DMSO-$d_6$) δ ppm 1.27-1.41 (m, 4H), 1.48 (d, J=6.6 Hz, 6H), 1.51-1.63 (m, 4H), 3.38 (quin, J=6.6 Hz, 1H), 4.91 (spt, J=6.5 Hz, 1H), 7.15 (t, J=8.9 Hz, 2H), 7.48 (br. s., 1H), 7.71 (d, J=9.0 Hz, 1H), 7.74 (dd, J=9.0, 1.6 Hz, 1H), 7.76 (dd, J=9.0, 4.8 Hz, 2H), 8.61 (dd, J=1.5, 0.7 Hz, 1H), 9.34 (s, 1H).

Compound 8

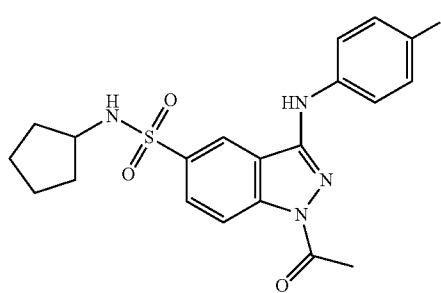

Compound 5 (600 mg, 1.6 mmol) was dissolved in 1,4-dioxane (50 mL) cyclopropylboronic acid (690 mg, 8 mmol), Cu (OAc)$_2$ (181 mg, 8 mmol), $Cs_2CO_3$ (0.45 g, 5 mmol) and DMAP (200 mg, 1.634 mmol) were added. The mixture was stirred at 50° C. overnight. The solvent was removed in vacuo and the obtained residue was purified by high performance liquid chromatography (Column: Phenomenex Synergi Diamonsil 150*20 mm*5 um. Method: From 25% to 55% B in A. A: $H_2O$+0.1% TFA B: $CH_3CN$. Flow Rate (mL/min): 40). The pure fractions were collected and basified to pH=7 with saturated aqueous $NaHCO_3$. The volatiles were removed in vacuo. The aqueous layer was extracted with ethyl acetate (3×20 mL). The combined organic layers were washed with brine and dried over $Na_2SO_4$. The solvent was removed in vacuo and the obtained residue was suspended in water (5 mL) and $CH_3CN$ (2 mL). The mixture was lyophilized to dryness resulting in compound 8 (380 mg). Method E; Rt: 4.74 min. m/z: 415.1 (M+H)$^+$ Exact mass: 414.2. $^1$H NMR (600 MHz, DMSO-$d_6$) δ ppm 1.11-1.15 (m, 4H), 1.21-1.41 (m, 4H), 1.45-1.66(m, 4H), 3.39 (sxt, J=6.7 Hz, 1H), 3.61-3.68 (m, 1H), 7.15 (t, J=8.9 Hz, 2H), 7.51 (d, J=6.9 Hz, 1H), 7.69 (dd, J=8.9, 0.5 Hz, 1H), 7.75 (dd, J=9.0, 4.8 Hz, 1H), 7.79 (dd, J=8.9, 1.7 Hz, 2H), 8.62 (dd, J=1.8, 0.6 Hz, 1H), 9.34 (s, 1H).

Compound 9

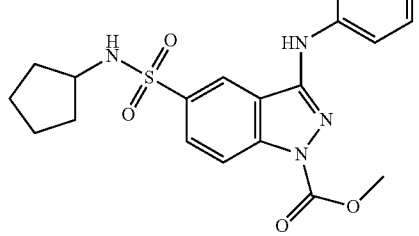

Compound 5 (1.5 g, 4 mmol) was dissolved in $Ac_2O$ (50 mL). The mixture was stirred at 110° C. for 12 hours. The solvent was removed in vacuo, the obtained residue was washed with $H_2O$ (5 mL) and dichloromethane (5 mL) and dried in vacuo resulting in compound 9 (1.35 g). Method B; Rt: 4.70 min. m/z: 417.2 (M+H)$^+$ Exact mass: 416.1. $^1$H NMR (600 MHz, DMSO-$d_6$) δ ppm 9.81 (1H, s), 8.80 (1H, dd, J=1.8, 0.5 Hz), 8.43 (1H, dd, J=8.8, 0.5 Hz), 8.03 (1H, dd, J=8.8, 1.8 Hz), 7.79-7.87 (2H, m), 7.71 (1H, d, J=7.0 Hz), 7.18 (2H, t, J=9.0 Hz), 3.45 (1H, sxt, J=7.0 Hz), 2.66 (3H, s), 1.55-1.63 (2H, m), 1.45-1.56 (2H, m), 1.32-1.39 (2H, m), 1.24-1.32 (2H, m)

Compound 10

Compound 5 (1.5 g, 4 mmol) was dissolved in DMF (20 mL). NaH (0.48 g, 20 mmol) was added to the mixture at 0° C. Methyl carbonochloridate (1.89 g, 20 mmol) was added dropwise at 0° C. The mixture was stirred at 25° C. for 12 hours. $H_2O$ (5 mL) was added dropwise at 0° C. The solvent was removed in vacuo. The residue was washed with $H_2O$ (5 mL), dichloromethane (10 mL) and N, N-dimethylformamide (5 mL) and dried in vacuo resulting in compound 10 (1.33 g). Method B; Rt: 4.54 min. m/z: 433.1 (M+H)$^+$ Exact mass: 432.1. $^1$H NMR (600 MHz, DMSO-$d_6$) δ ppm 9.97 (1H, s), 8.92 (1H, dd, J=1.8, 0.6 Hz), 8.28 (1H, d, J=8.8 Hz), 8.07 (1H, dd, J=8.8, 1.8 Hz), 7.88-7.95 (2H, m), 7.79 (1H, d, J=7.0 Hz), 7.18-7.28 (2H, m), 4.05 (3H, s), 3.45-3.55 (1H, m), 1.58-1.66 (2H, m), 1.49-1.58 (2H, m), 1.23-1.42 (4H, m).

Compound 11

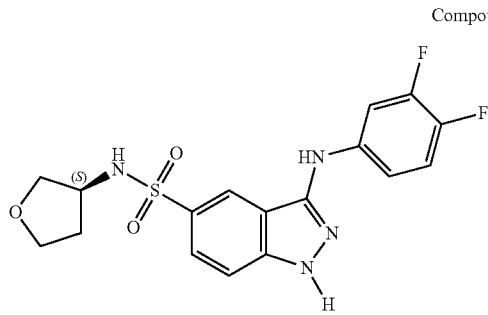

Prepared similarly as described for compound 5 using (3S)-tetrahydrofuran-3-amine hydrochloride instead of cyclopentylamine and 3,4-difluoroaniline instead of 4-fluoroaniline. Method D; Rt: 5.5 min. m/z: 395.2 (M+H)$^+$ Exact mass: 394.1.

Compound 12

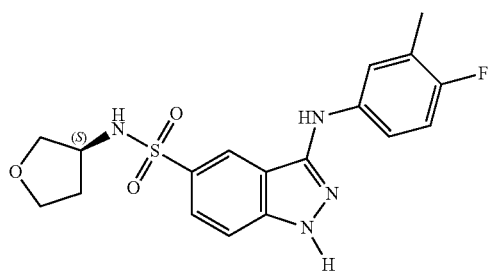

Prepared similarly as described for compound 11 using 4-fluoro-3-methyl-aniline instead of 3,4-difluoroaniline. Method B; Rt: 4.15 min. m/z: 391.2 (M+H)$^+$ Exact mass: 390.1.

Compound 13

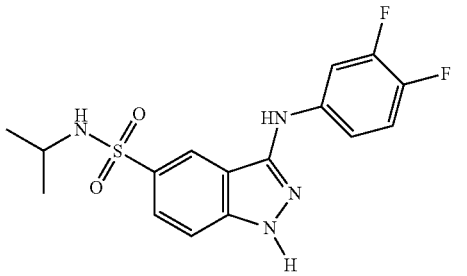 [SMILES: CC(C)NS(=O)(=O)c1ccc2[nH]nc(Nc3ccc(F)c(F)c3)c2c1]

To a solution of 3-cyano-4-fluorobenzenesulfonyl chloride (3 g, 13.7 mmol) and isopropylamine (1.211 g, 20.49 mmol) in CH$_2$Cl$_2$ (30 mL), N,N-Diisopropylethylamine (3.53 g, 27.3 mmol) was added. The resulting mixture was stirred at 18° C. for 2 hours. The reaction mixture was washed with 1 N HCl (25 mL) and saturated aqueous NaHCO$_3$ (25 mL), dried over Na$_2$SO$_4$ and concentrated in vacuo resulting in crude 3-cyano-4-fluoro-N-isopropyl-benzenesulfonamide (3.4 g). To a solution of crude 3-cyano-4-fluoro-N-isopropyl-benzenesulfonamide (2.9 g) in 2-propanol (30 mL) was added hydrazine (0.77 g, 23.9 mmol). The resulting mixture was refluxed at 110° for 1 hour. The mixture was concentrated under reduced pressure resulting in crude 3-amino-N-isopropyl-1H-indazole-5-sulfonamide (4.1 g). A solution of copper (II) acetate (714 mg, 3.93 mmol) in CH$_2$Cl$_2$ (15 mL) was stirred for 5 minutes. Crude 3-amino-N-isopropyl-1H-indazole-5-sulfonamide (1 g), 3,4-difluorophenylboronic acid (620.9 mg, 3.9 mmol) and N,N-diisopropylethylamine (508 mg, 3.9 mmol) was added. The resulting mixture was stirred and refluxed at 50° C. under O$_2$ overnight. The organic layer was separated and the aqueous layer was extracted with dichloromethane (20 mL). The combined organic layers were dried over Na$_2$SO$_4$ and concentrated under reduced pressure resulting in crude compound 13. The crude product was purified by preparative high-performance liquid chromatography on reversed phase (eluent: CH$_3$CN in H$_2$O (0.05% NH$_3$.H$_2$O) from 38% to 68%, v/v). The pure fractions containing compound 13 were collected and the organics were removed in vacuo. The aqueous layer was lyophilized to dryness, resulting in compound 13 (114 mg). Method B; Rt: 4.23 min. m/z: 367 (M+H)$^+$ Exact mass: 366.1.

Compound 14

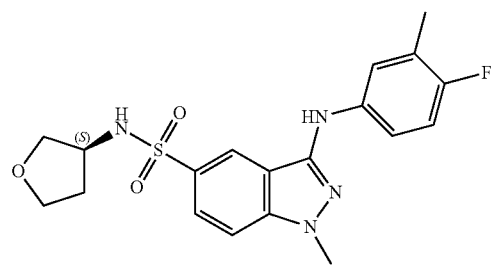

Prepared similarly as described for compound 12 using methylhydrazine instead of hydrazine hydrate. Method D; Rt: 5.88 min. m/z: 405.3 (M+H)$^+$ Exact mass: 404.1.

Compound 15

Prepared similarly as described for compound 5 using isopropylamine instead of cyclopentylamine, 3-(difluoromethyl)-4-fluoro-aniline instead of 4-fluoroaniline and methylhydrazine instead of hydrazine hydrate. Method B; Rt: 4.71 min. m/z: 413.3 (M+H)$^+$ Exact mass: 412.1. $^1$H NMR (400 MHz, DMSO-d$_6$) δ ppm 0.93 (d, J=6.5 Hz, 6H) 3.08-3.28 (m, 1H) 3.97 (s, 3H) 7.23 (t, J=54.2 Hz, 1H) 7.28-7.42 (m, 1H) 7.46 (br. s, 1H) 7.63-7.72 (m, 1H) 7.72-7.84 (m, 1H) 7.91-8.04 (m, 2H) 8.62 (s, 1H) 9.59 (s, 1H).

Compound 16

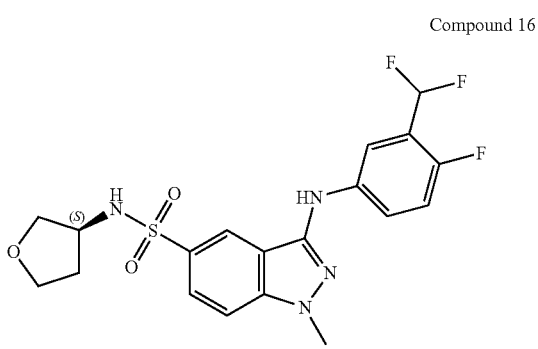

Prepared similarly as described for compound 15 using (3S)-tetrahydrofuran-3-amine hydrochloride instead of isopropylamine Method D; Rt: 5.84 min. m/z: 441.2 (M+H)$^+$ Exact mass: 440.1.

Compound 17

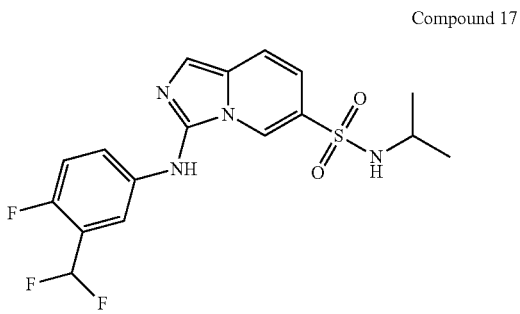

3-(difluoromethyl)-4-fluoro-aniline (1000 mg, 6.2 mmol), 1,1'-thiocarbonyldi-2(1 h)-pyridone (1.72 g, 7.4 mmol) and CH$_2$Cl$_2$ were sequentially added to a 20 mL vial at 25° C. The mixture was heated by microwave irradiation at 70° C. for 1 hour. The mixture was quenched with water, extracted with dichloromethane (20 mL). The organic layer was separated and concentrated in vacuo. The obtained residue (1.8 g), containing 2-(difluoromethyl)-1-fluoro-4-isothiocyanato-benzene was used without purification. 6-chloro-N-isopropyl-pyridine-3-sulfonamide (4 g, 17.0 mmol), zinc cyanide (4.0 g, 34 mmol), palladium(II) acetate (381 mg, 1.7 mmol), 1,1'-bis(diphenylphosphino)ferrocene (942 mg, 1.7 mmol) and N,N-dimethylacetamide (50 mL) were sequentially added at 25° C. to a 250 mL flask. The mixture was warmed to 60° C. and stirred for 2 hours under nitrogen atmosphere. The mixture was quenched with water, extracted with dichloromethane (50 mL). The organic layer was separated and concentrated in vacuo. The crude product was purified by silica gel column chromatography (petroleum ether and ethyl acetate (3:1) resulting in 6-cyano-N-isopropyl-pyridine-3-sulfonamide (3.4 g) 6-cyano-N-isopropyl-pyridine-3-sulfonamide. 6-cyano-N-isopropyl-pyridine-3-sulfonamide (2 g) and nickel (skeletal, molybdenum promoted, 280 mg)) were dissolved in methanol (2 mL). The mixture was stirred in a autoclave (degassed with hydrogen gas for three times). The mixture was stirred at 50° C. for 12 hours under hydrogen atmosphere (50 psi). The mixture was filtered off and the volatiles were removed in vacuo The crude 6-(aminomethyl)-N-isopropyl-pyridine-3-sulfonamide (1.5 g) was used in the next step without purification. Crude 6-(aminomethyl)-N-isopropyl-pyridine-3-sulfonamide (1.5 g) and 2-(difluoromethyl)-1-fluoro-4-isothiocyanato-benzene (1.3 g) were dissolved in toluene (20 mL). The mixture was stirred at 120° C. for 12 hours. The solvent was removed in vacuo. The obtained residue was purified by silica gel column chromatography (eluent: petroleum ether: ethyl acetate=3:1), resulting in 1-[3-(difluoromethyl)-4-fluoro-phenyl]-3-[[5-(isopropylsulfamoyl)-2-pyridyl]methyl]thiourea (0.9 g). 1-[3-(difluoromethyl)-4-fluoro-phenyl]-3-[[5-(isopropylsulfamoyl)-2-pyridyl]methyl]thiourea (0.9 g) and DCC (0.9 g, 4.2 mmol) were dissolved in toluene. The mixture was stirred at 120° C. for 12 hours. The solvent was removed in vacuo and the obtained residue was purified by high performance liquid chromatography on reversed phase (mobile phase: CH3CN in water (0.1% TFA) from 0 to 30%). The pure fractions were collected and neutralized with solid NaHCO$_3$. The organic solvent was removed in vacuo. The formed precipitate was filtered, washed with H$_2$O (5 mL) and dried under high vacuum. The residue was suspended in water (5 mL) and the aqueous layer was lyophilized to dryness, resulting in compound 17 (290 mg). Method B; Rt: 3.87 min. m/z: 399.3 (M+H)$^+$ Exact mass: 398.1. $^1$H NMR (400 MHz, DMSO-d$_6$) δ ppm 0.99 (d, J=6.3 Hz, 6H) 3.20-3.33 (m, 1H) 6.72 (d, J=9.5 Hz, 1H) 7.20 (t, J=53.5 Hz, 1H) 7.23-7.37 (m, 2H) 7.56 (d, J=9.5 Hz, 1H) 7.66-7.85 (m, 2H) 7.93 (d, J=3.3 Hz, 1H) 8.75 (s, 1H) 9.56 (br. s., 1H)

Compound 18

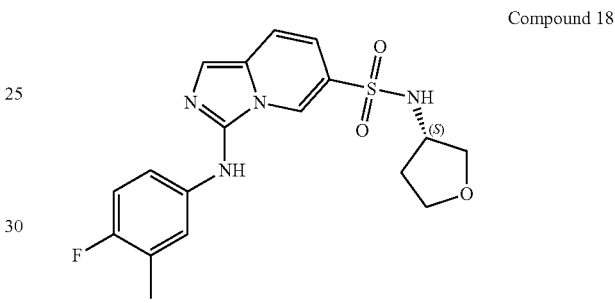

2-chloropyridine-5-sulfonyl chloride (10 g, 47.1 mmol) and (S)-3-aminotetrahydrofuran tosylate (3.3 g, 38 mmol) were sequentially added at 0° C., to CH$_2$Cl$_2$ (200 mL) triethylamine was slowly added. The mixture was warmed to 25° C. and stirred for 2 hours. The mixture was quenched with water, extracted with dichloromethane (100 mL). The organic layer was separated and concentrated under vacuum. The crude product was purified by column chromatography eluted by petroleum ether and ethyl acetate (3:1) resulting in 6-chloro-N-[(3S)-tetrahydrofuran-3-yl]pyridine-3-sulfonamide.
Compound 18 was prepared similarly as described for compound 17, using 6-chloro-N-[(3S)-tetrahydrofuran-3-yl]pyridine-3-sulfonamide instead of 6-chloro-N-isopropyl-pyridine-3-sulfonamide and 4-fluoro-3-methylphenyl isothiocyanate instead of 2-(difluoromethyl)-1-fluoro-4-isothiocyanato-benzene. Method B, Rt: 3.35 min. m/z: 391.3 (M+H)$^+$ Exact mass: 390.1.

Compound 19

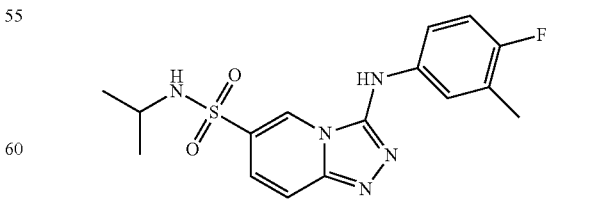

6-chloro-N-isopropyl-pyridine-3-sulfonamide (1.03 g, 4.38 mmol) and hydrazine (1.54 g, 48.2 mmol) in EtOH (5 mL) was heated at 85° C. during 2 hours. The reaction mixture was cooled in an icebath during 1 hour. The formed white crystals were filtered off, washed with cold ethanol (5 mL) and dried in vacuo at 50° C. during 2 hours, resulting in 6-hydrazino-N-isopropyl-pyridine-3-sulfonamide (694 mg). A solution of 4-fluoro-3-methylphenyl isothiocyanate (477 mg, 2.86 mmol) in THF (10 mL) was added portionwise during 3 minutes to a solution of 6-hydrazino-N-isopropyl-pyridine-3-sulfonamide (679 mg, 2.86 mmol) in THF and stirred 90 minutes. The reaction mixture was concentrated and the resulting white powder was crystallised from acetonitrile/water. The white crystals (844 mg) were filtered off and dried in vacuo at 50° C. To a solution of part of the white crystals (738 mg) in THF (50 mL), NEt$_3$ (0.62 mL, 4.45 mmol) was added, followed by 2-chloro-1-methylpyridinium iodide (569 mg, 2.23 mmol) and stirred. The reaction mixture was left standing overnight and next concentrated in vacuo. The obtained residue was stirred in CH$_2$Cl$_2$/1M HCl 100 mL/100 mL. A yellow precipitate was filtered off, dissolved in a minimal amount of methanol and charged onto a Waters Porapak CX 5 g cartridge (eluted twice with methanol and the product eluted with 2 volumes NH$_3$ 7 M/CH$_3$OH). After concentration of the product fraction in vacuo, the obtained residue was subjected to silica gel column chromatography (2 to 10% CH$_3$OH in dichloromethane), resulting in compound 19 (75 mg). Method F, Rt: 1.59 min. m/z: 364.1 (M+H)$^+$ Exact mass: 363.1. $^1$H NMR (400 MHz, DMSO-d$_6$) δ ppm 1.01 (d, J=6.6 Hz, 6H), 2.26 (d, J=1.5 Hz, 3H), 3.25-3.40 (1H, proton signal under H$_2$O-peak according to 2D-cosy), 7.12 (t, J=9.1 Hz, 1H), 7.36 (dd, J=9.7, 1.5 Hz, 1H), 7.52-7.59 (m, 1H), 7.65 (dd, J=6.8, 2.6 Hz, 1H), 7.76 (dd, J=9.7, 0.9 Hz, 1H), 8.04 (br. s, 1H), 9.07 (d, J=1.1 Hz, 1H), 9.65 (br. s, 1H).

BIOLOGICAL EXAMPLES

Anti-HBV Activity of Compounds of Formula (I)

The anti-HBV activity was measured using a stable transfected cell line, HepG2.2.15. This cell line was described to secrete relatively consistent high levels of HBV virion particles, which have been shown to cause both acute and chronic infection and disease in chimpanzees. For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was also tested using HepG2 cells, incubated for 4 days in the presence of compounds. The viability of the cells was assessed using a Resazurin assay. Results are displayed in Table 1.

TABLE 1

| STRUCTURE | Compound nr. | HBV - HepG2.15; EC50 (µM) | HepG2 117 EC50 (µM) | HepG2 4 days CC50 (µM) |
|---|---|---|---|---|
| [structure: indazole with F-phenyl-NH and sulfonamide-N-cyclohexyl] | 3 | 1.0 | 4.6 | >25 |
| [structure: benzisoxazole with F-phenyl-NH and sulfonamide-N-cyclohexyl] | 4 | 0.74 | 1.2 | >25 |
| [structure: indazole with F-phenyl-NH and sulfonamide-N-cyclopentyl] | 5 | 1.0 | 1.8 | >25 |

TABLE 1-continued
| STRUCTURE | Compound nr. | HBV - HepG2.15; EC50 (µM) | HepG2 117 EC50 (µM) | HepG2 4 days CC50 (µM) |
|---|---|---|---|---|
| 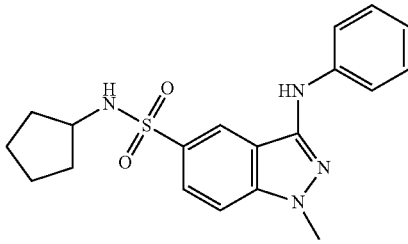 | 6 | 0.49 | 0.82 | >25 |
| 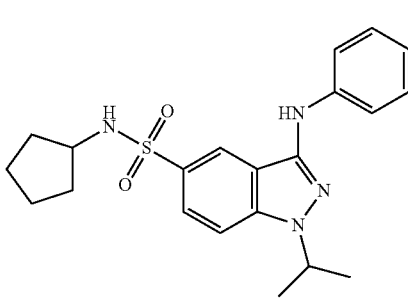 | 7 | >50 | >25 | >25 |
| 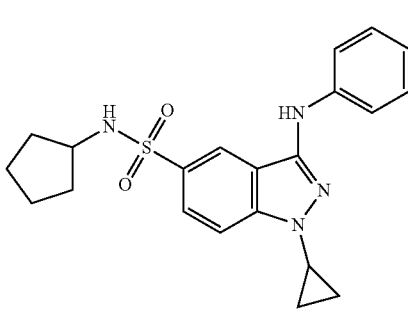 | 8 | 0.21 | 0.62 | >25 |
| 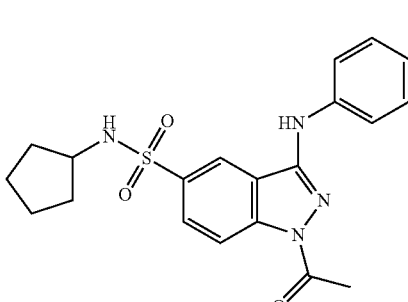 | 9 | >50 | 18.4 | >25 |
| 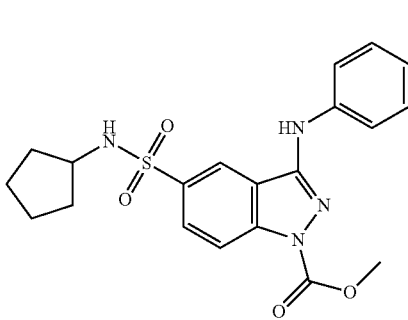 | 10 | 46.5 | >25 | >25 |

TABLE 1-continued

| STRUCTURE | Compound nr. | HBV - HepG2.15; EC50 (μM) | HepG2 117 EC50 (μM) | HepG2 4 days CC50 (μM) |
| --- | --- | --- | --- | --- |
| (structure) | 11 | 3.3 | 12.4 | >25 |
| (structure) | 12 | 5.2 | >25 | >25 |
| (structure) | 13 | 8.9 | >25 | >25 |
| (structure) | 14 | 1.1 | 8.5 | >25 |
| (structure) | 15 | 0.44 | 2.8 | >25 |

TABLE 1-continued

| STRUCTURE | Compound nr. | HBV - HepG2.15; EC50 (µM) | HepG2 117 EC50 (µM) | HepG2 4 days CC50 (µM) |
|---|---|---|---|---|
| 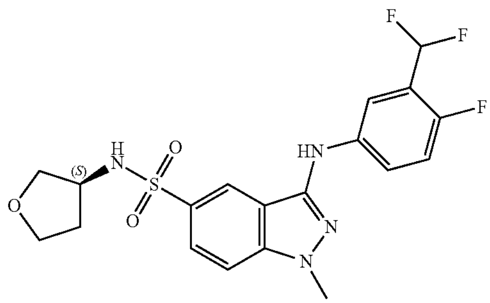 | 16 | 1.3 | 4.5 | >25 |
| 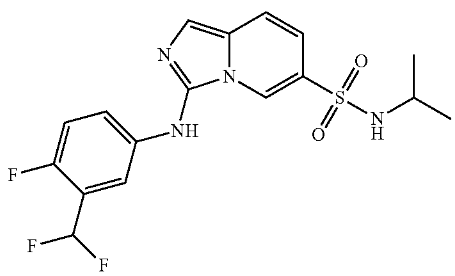 [SMILES: CC(C)NS(=O)(=O)c1ccc2cnc(Nc3ccc(F)c(C(F)F)c3)n2c1] | 17 | 0.56 | 14.2 | >25 |
| 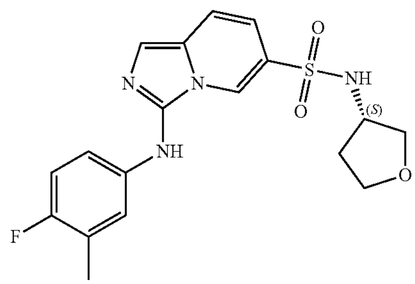 | 18 | 1.7 | >25 | >25 |
| 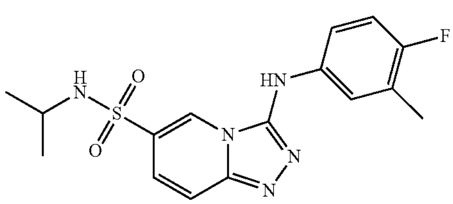 [SMILES: Cc1cc(Nc2nnc3ccc(S(=O)(=O)NC(C)C)cn23)ccc1F] | 19 | 1.2 | 3.4 | >25 |

The invention claimed is:

1. A compound of Formula (I)

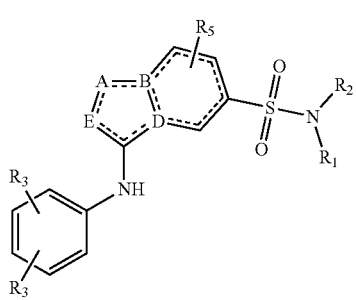

a stereoisomer, tautomeric form thereof, a pharmaceutically acceptable salt, or a solvate thereof, wherein:
A is N, C or O;
B is C or N;
D is C or N;
E is C or N;
wherein if A and E are either N or C, they are optionally substituted with $R_4$;
$R_1$ is hydrogen or $C_1$-$C_3$alkyl;
$R_2$ is $C_1$-$C_6$alkyl, $C_1$-$C_3$alkyl-$R_6$, benzyl, or a 3-7 membered saturated ring optionally containing one or more heteroatoms each independently selected from the group consisting of O, S and N, said $C_1$-$C_6$alkyl or a 3-7 membered saturated ring optionally being substituted with one or more substituents each independently selected from the group consisting of hydrogen, halo, $C_1$-$C_3$alkyloxy, $C_1$-$C_4$alkyl, OH, CN, $CFH_2$, $CF_2H$ and $CF_3$;

or $R_1$ and $R_2$ together with the nitrogen to which they are attached form a 5-7 membered saturated ring optionally being substituted with one or more substituents each independently selected from the group consisting of hydrogen, halogen, $C_1$-$C_4$alkyloxy, $C_1$-$C_3$alkyl, OH, CN, $CFH_2$, $CF_2H$ and $CF_3$;

each $R_3$ is independently selected from the group consisting of hydrogen, halo, $C_1$-$C_4$alkyloxy, $C_1$-$C_4$alkyl, OH, CN, $CFH_2$, $CF_2H$, $CF_3$ and a 3-5 membered saturated ring optionally containing one or more heteroatoms each independently selected from the group consisting of O and N;

$R_4$ is hydrogen, $C_1$-$C_4$alkyl, $C_3$-$C_5$cycloalkyl, —(C=O)$C_1$-$C_4$-alkyl, or —(C=O)—$C_1$-$C_3$alkyloxy; or if A or E is C, then $R_4$ is hydrogen, halogen, $C_1$-$C_4$alkyl, $C_3$-$C_5$cycloalkyl, —(C=O)$C_1$-$C_4$-alkyl, —(C=O)—$C_1$-$C_3$alkyloxy;

$R_5$ is hydrogen or halogen; and $R_6$ is a 3-7 membered saturated ring optionally containing one or more heteroatoms each independently selected from the group consisting of O, S and N, said 3-7 membered saturated ring optionally being substituted with one or more substituents each independently selected from the group consisting of hydrogen, halo, $C_1$-$C_3$alkyloxy, $C_1$-$C_4$alkyl, OH, CN, $CFH_2$, $CF_2H$, and $CF_3$.

2. A compound as claimed in claim 1, wherein $R_2$ is $C_1$-$C_3$alkyl-$R_6$ or $C_4$-$C_7$cycloalkyl, optionally being substituted with one or more substituents each independently selected from the group consisting of hydrogen, halo, $C_1$-$C_3$alkyloxy, $C_1$-$C_4$alkyl, OH, CN, $CFH_2$, $CF_2H$, $CF_3$ and wherein $R_6$ is a $C_4$-$C_7$ cycloalkyl, optionally being substituted with one or more substituents each independently selected from the group consisting of hydrogen, halo, $C_1$-$C_3$alkyloxy, $C_1$-$C_4$alkyl, OH, CN, $CFH_2$, $CF_2H$, $CF_3$.

3. A compound as claimed in claim 1, wherein at least one $R_3$ is independently selected from hydrogen, halogen, $C_1$-$C_4$alkyl, or a 3-5 membered saturated ring optionally containing one or more heteroatoms each independently selected from the group consisting of O and N.

4. A compound as claimed in claim 1, wherein said compound of Formula (I) is a compound of Formula (I-I) or (I-II)

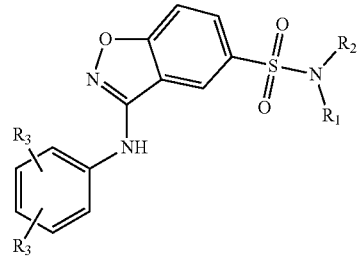

(I-I)

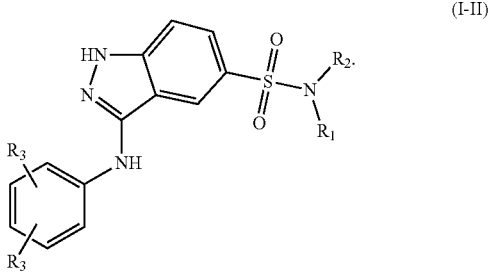

(I-II)

5. A compound as claimed in claim 1, wherein $R_2$ is $C_5$-cycloalkyl or $C_6$-cycloalkyl, optionally being substituted with one or more substituents each independently selected from the group consisting of hydrogen, halo, and $C_1$-$C_4$alkyl.

6. A compound as claimed in claim 1, wherein at least one $R_3$ is independently selected from the group consisting of fluoro, $C_1$-$C_3$alkyl and cyclopropyl.

7. A compound as claimed in claim 1, wherein $R_1$ is hydrogen or methyl.

8. A compound as claimed in claim 1, wherein $R_4$ is hydrogen.

9. A pharmaceutical composition comprising a compound as claimed in claim 1, and a pharmaceutically acceptable carrier.

10. A method of treating an HBV infection in a mammal, comprising the administration of a therapeutically effective amount of at least one compound as claimed in claim 1.

11. A product comprising a compound of Formula (I) as claimed in claim 1, and another HBV inhibitor, as a combined preparation for simultaneous, separate or sequential use in the treatment of HBV infections.

\* \* \* \* \*